US006824266B2

(12) United States Patent
Jethmalani et al.

(10) Patent No.: US 6,824,266 B2
(45) Date of Patent: Nov. 30, 2004

(54) LENSES CAPABLE OF POST-FABRICATION POWER MODIFICATION

(75) Inventors: Jagdish M. Jethmalani, Pasadena, CA (US); Daniel M. Schwartz, San Francisco, CA (US); Julia A. Kornfield, Pasadena, CA (US); Robert H. Grubbs, South Pasadena, CA (US); Christian A. Sandstedt, Pasadena, CA (US)

(73) Assignees: California Institute of Technology, Pasadena, CA (US); Regents of the University of California, Oakland, CA (US)

( * ) Notice: Subject to any disclaimer, the term of this patent is extended or adjusted under 35 U.S.C. 154(b) by 0 days.

(21) Appl. No.: 10/358,065

(22) Filed: Feb. 3, 2003

(65) Prior Publication Data

US 2003/0173691 A1 Sep. 18, 2003

Related U.S. Application Data

(63) Continuation of application No. 10/177,722, filed on Jun. 18, 2002, which is a continuation of application No. 09/416,044, filed on Oct. 8, 1999, now Pat. No. 6,450,642.
(60) Provisional application No. 60/115,617, filed on Jan. 12, 1999, provisional application No. 60/132,871, filed on May 5, 1999, and provisional application No. 60/140,298, filed on Jun. 17, 1999.

(51) Int. Cl.$^7$ ................................................. G02C 7/02
(52) U.S. Cl. ...................................... 351/159; 623/6.11
(58) Field of Search ................................. 351/159–177, 351/160 R, 160 H, 219; 623/5.16–6.17; 264/1.1, 485, 488; 526/279; 522/99, 182; 252/586, 582

(56) References Cited

U.S. PATENT DOCUMENTS 3,955,015 A    5/1976    Ohtsuka et al.
4,104,204 A    8/1978    Williams (List continued on next page.)

FOREIGN PATENT DOCUMENTS

DE    3605512 A1    8/1986
EP    0472384 A2    2/1992

(List continued on next page.)

OTHER PUBLICATIONS

PCT Written Opinion dated May 17, 2001 from corresponding International Application No. PCT/US99/23728 filed Oct. 18, 1999.

(List continued on next page.)

*Primary Examiner*—George Manuel
(74) *Attorney, Agent, or Firm*—Christie, Parker & Hale, LLP

(57) ABSTRACT

The present invention relates to lenses that are capable of post-fabrication power modifications. In general, the inventive lenses comprise (i) a first polymer matrix and (ii) a refraction modulating composition that is capable of stimulus-induced polymerization dispersed therein. When at least a portion of the lens is exposed to an appropriate stimulus, the refraction modulating composition forms a second polymer matrix. The amount and location of the second polymer matrix may modify a lens characteristic such as lens power by changing its refractive index and/or by altering its shape. The inventive lenses have a number of applications in the electronics and medical fields as data storage means and as medical lenses, particularly intraocular lenses, respectively.

35 Claims, 6 Drawing Sheets

U.S. PATENT DOCUMENTS

| | | | |
|---|---|---|---|
| 4,173,474 A | | 11/1979 | Tanaka et al. |
| 4,173,475 A | | 11/1979 | Chandross et al. |
| 4,260,725 A | | 4/1981 | Keogh et al. |
| 4,330,383 A | | 5/1982 | Ellis et al. |
| 4,575,373 A | | 3/1986 | Johnson |
| 4,685,921 A | | 8/1987 | Peyman |
| 4,787,903 A | | 11/1988 | Grendahl |
| 4,790,847 A | | 12/1988 | Woods |
| 4,816,031 A | | 3/1989 | Pfoff |
| 4,846,172 A | | 7/1989 | Berlin |
| 4,921,589 A | | 5/1990 | Yates et al. |
| 4,942,112 A | | 7/1990 | Monroe et al. |
| 5,066,301 A | | 11/1991 | Wiley |
| 5,141,678 A | | 8/1992 | Blum |
| 5,171,266 A | | 12/1992 | Wiley et al. |
| 5,173,381 A | | 12/1992 | Natansohn et al. |
| 5,213,825 A | | 5/1993 | Shimizu et al. |
| 5,258,024 A | | 11/1993 | Chavel et al. |
| 5,288,293 A | | 2/1994 | O'Donnell, Jr. |
| 5,296,305 A | | 3/1994 | Baude et al. |
| 5,443,506 A | | 8/1995 | Garabet |
| 5,470,662 A | | 11/1995 | Weber et al. |
| 5,480,428 A | | 1/1996 | Fedorov et al. |
| 5,529,861 A | | 6/1996 | Redfield |
| 5,549,668 A | | 8/1996 | O'Donnell, Jr. |
| 5,623,002 A | | 4/1997 | Nomura et al. |
| 5,684,636 A | | 11/1997 | Chow et al. |
| 5,702,846 A | | 12/1997 | Sato et al. |
| 5,725,575 A | | 3/1998 | O'Donnell, Jr. |
| 5,728,155 A | | 3/1998 | Anello et al. |
| 5,728,156 A | | 3/1998 | Gupta et al. |
| 5,744,267 A | | 4/1998 | Meerholz et al. |
| 5,762,836 A | | 6/1998 | Bos et al. |
| 5,807,906 A | | 9/1998 | Bonvallot et al. |
| 5,858,585 A | | 1/1999 | Haarer et al. |
| 5,886,764 A | * | 3/1999 | Engardio et al. ........... 351/177 |
| 5,892,601 A | | 4/1999 | Curtis et al. |
| 5,920,536 A | | 7/1999 | Campbell et al. |
| 5,943,145 A | | 8/1999 | Curtis et al. |
| 5,964,802 A | | 10/1999 | Anello et al. |
| 5,984,962 A | | 11/1999 | Anello et al. |
| 5,995,251 A | | 11/1999 | Hesselink et al. |
| 5,998,096 A | | 12/1999 | Umemoto et al. |
| 6,046,290 A | | 4/2000 | Berneth et al. |
| 6,154,432 A | | 11/2000 | Faruqi et al. |
| 6,174,464 B1 | * | 1/2001 | Garrity ....................... 252/586 |
| 6,271,281 B1 | | 8/2001 | Liao et al. |

FOREIGN PATENT DOCUMENTS

| | | |
|---|---|---|
| EP | 0689067 A2 | 12/1995 |
| EP | 0689067 A3 | 4/1997 |
| JP | 60175009 | 9/1985 |
| JP | 61027501 | 2/1986 |
| JP | 05096553 | 4/1993 |
| JP | 07281426 | 10/1995 |
| JP | 08101499 | 4/1996 |
| JP | 08101502 | 4/1996 |
| JP | 08101503 | 4/1996 |
| JP | 11202740 | 7/1999 |
| WO | WO-93/21245 A1 | 2/1993 |
| WO | WO-95/17460 A1 | 6/1995 |
| WO | WO-98/05272 A1 | 2/1998 |
| WO | WO-98/27863 A1 | 7/1998 |
| WO | WO-99/26112 A1 | 5/1999 |
| WO | WO-00/41650 A1 | 7/2000 |
| WO | WO-01/21061 A1 | 3/2001 |
| WO | WO-01/71411 A2 | 9/2001 |
| WO | WO-01/86647 A3 | 11/2001 |
| WO | WO-01/86647 A2 | 11/2001 |

OTHER PUBLICATIONS

PCT International Preliminary Examination Report dated Oct. 29, 2001 from corresponding International Application No. PCT/US99/23728 filed Oct. 13, 1999.

PCT International Search Report dated May 22, 2000 from corresponding International Application No. PCT/US99/23728 filed Oct. 13, 1999.

American National Standard for Safe Use of Lasers: B. Criteria for Exposures of Eye and Skin; American National Standard; 1993; pp. 31–43; Laser Insitute of America; Orlando, Florida.

Holographic Optical Elements, National Technical Information Service Publication AD760561, Jan. 1973., 170 pages, U.S. Department of Commerce.

Allen et al., Synthesis, photopolymerization and photochemistry of novel polysiloxane photoinitiators; J. Photochem. Photobiol. A: Chem.; 1991; pp. 125–139; vol. 62; Elsevier Sequoia, Lausanne.

Apple et al., Irreversible Silicone Oil Adhesion to Silicone Intraocular Lenses—A Clinicopathologic Analysis; Ophthalmology; Oct. 1996; pp. 1555–1562; vol. 103; No. 10.

Baltus et al., Solubility and Diffusivity of Cyclic Oligomers in Poly(dimethylsiloxane) Using Capillary Column Inverse Gas Chromatography, Macromolecules; 1993; pp. 5651–5656; vol. 26; American Chemical Society.

Barakat; General Diffraction Theory of Optical Aberration Tests, from the Point of View of Spatial Filtering; Journal of the Optical Society of America; Nov. 1969; pp. 1432–1439; vol. 59; No. 11.

Bennett et al.; Clinical Visual Optics—3rd Edition, Chapters 4 & 5; 1998; pp. 62–92; Butterworth–Heinemann Ltd.; Woburn, Massachusetts.

Brandser et al., Accuracy of IOL calculation in cataract surgery; Acta Opthalmologica Scandinavica; 1997; pp. 162–165; vol. 75; No. 2.

Bräuchle et al., Holographic Spectroscopy and Holographic Information Recording in Polymer Matrices; Lasers in Polymer Science and Technology: Applications; 1990; pp. 181–209; vol. III, Ed. Jean–Pierre Fouassier, Jan F. Rabek, CRC Press.

Canabal et al.; Automatic processing in moiré deflectometry by local fringe direction calculation: Applied Optics; Sep. 1, 1998; pp. 5894–5901; vol. 37, No. 25: Optical Society of America.

Chang et al.; An Improved Technique of Measuring the Focal Length of a Lens; Optics Communications; Oct. 15, 1989; pp. 257–262; vol. 73, No. 4; Elsevier Science Publishers B.V.; North Holland.

Cornejo et al.; Ronchi Test of Aspherical Surfaces, Analysis, and Accuracy; Applied Optics; Aug. 1970; pp. 1897–1901; vol. 9, No. 8.

Cornejo–Rodriguez; 9/Ronchi Test; Optical Shop Testing, 2d Ed.—Malacara–Doblado, D.; 1992; pp. 321–365; John Wiley & Sons, Inc., New York.

Decker et al.; High–Speed Polymerization of Acrylate Monomers By UV Irradiation; pp. 487–488.

Dreβ et al.; Volume Phase Gratings in DMPA–Doped Polymers: Applied Physics A; 1994; vol. 58; pp. 401–405;Springer–Verlag.

Ducharme et al., Observation of the Photorefractive Effect in a Polymer, Physical Review Letters, Apr. 8, 1991, pp. 1846–1849, vol. 66, No. 14, American Physical Society.

Duke–Elder et al., System of Ophthalmology—Ophthalmic Optics and Refraction, Chapters II–IV, 1970, pp. 26–153, vol. V, Henry Kimpton, London.

Fouassier et al.; Photopolymers for laser imaging and holographic recording: design and reactivity of photosensitizers; Optical Engineering; Jan. 1996; vol. 35, No. 1; pp. 304–312.

Fouassier et al.; Visible Lasers Lights in Photoinduced Polymerization. VI. Thioxanthones and Ketocoumarins as Photoinitiators; Journal of Applied Polymer Science; 1992; vol. 44; pp. 1779–1786; John Wiley & Sons, Inc.

Gedde et al.; Sorption of Low Molar Mass Silicones in Silicone Elastomers; Polymer Engineering and Science; Aug. 1996, vol. 36, No. 16; pp. 2077–2082.

Goodman, Chapter 8/Wavefront–Reconstruction Imaging, or Holography, Introduction to Fourier Optics, 1968, pp. 198–273, McGraw–Hill, Inc., USA.

He et al.; Chain Extenstion of $\alpha$–$\omega$–Dihydroxy Polydimethylsiloxane: Simulation of the Linear Polycondensation Reaction; European Polymer Journal; 1991; pp. 449–453; vol. 27, No. 4/5; Pergamon Press plc; Great Britain.

He et al.; Competition Between Polycondensation of $\alpha$–$\omega$–Dihydroxy Polydimethylsiloxane and its Condensation with Alkoxy Silane: A Kinetic Approach; European Polymer Journal; 1988; pp. 1145–1148; vol. 24, No. 12; Pergamon Press plc; Great Britain.

Ingwall et al.; Hologram recording with a new photopolymer system; Optical Engineering; Oct. 1985; pp. 808–811; vol. 24, No. 5; Society of Photo–Optical Instrumentation Engineers.

Ingwall et al.; Mechanism of hologram formation in DMP–128 photopolymer; Optical Engineering; Jun. 1989; pp. 586–591; vol. 28, No. 6; Society of Photo–Optical Instrumentation Engineers.

Javitt et al., Outcomes of Cataract Extraction with Multifocal Intraocular Lens Implantation—Functional Status and Quality of Life; Ophthalmology; Apr. 1997; pp. 589–599; vol. 104; No. 4.

Kippelen et al., New highly efficient photorefractive polymer composite for optical–storage and image–processing applications, Electronics Letters, Oct. 14, 1993, pp. 1873–1874, vol. 29, No. 21.

Kloosterboer; Network Formation by Chain Crosslinking Photopolymerization and its Applications in Electronics; Advances in Polymer Science 84; 1988; pp. 1–61; Springer–Verlag Berlin Heidelberg.

Kunzler; Silicon Hydrogels for Contact Lens Application, Trends in Polymer Science; Feb. 1996; vol. 4, No. 2; pp. 52–59; Elsevier Science Ltd.

Kunzler et al.; Hydrogels Based on Hydrophilic Side–Chain Siloxanes; Journal of Applied Polymer Science; 1995; vol. 55; pp. 611–619; John Wiley & Sons, Inc.

Lai et al., Synthesis and Characterization of $\alpha,\omega$–Bis(4–hydroxybutyl) Polydimethylsiloxanes; Journal of Polymer Science; 1995; vol. 33; pp. 1773–1783; John Wiley & Sons, Inc.

Learning, Practice styles and preferences of ASCRS members—1996 survey.; J. Cataract Refract. Surg.; May 1997; pp. 527–535; vol. 23; ASCRS and ESCRS; Elsevier Science Inc.

Learning, *special report*—Practice styles and preferences of ASCRS members—1999 survey.; J. Cataract Refract. Surg.; Jun. 2000; pp. 913–921; vol. 26; ASCRS and ESCRS; Elsevier Science Inc.

Levi, New Compound Brightens Outlook for Photorefractive Polymers, Physics Today, Jan. 1995, pp. 17–19, vol. 48, No. 1, American Institute of Physics.

Liang et al., Objective measurement of wave aberrations of the human eye with the use of a Hartmann–Shack wavefront sensor, J. Optical Society of America, Jul. 1994, pp. 1949–1957, vol. 11, No. 7, Optical Society of America.

Liang et al., Supernormal vision and high–resolution retinal imaging through adaptive optics, J. Optical Society of America, Nov. 1997, pp. 2884–2892, vol. 14, No. 11, Optical Society of America.

Longhurst; Chapter II—The General Geometrical Theory of Optical Systems; Geometrical And Physical Optics—2nd Edition; 1967; pp. 16–41; John Wiley & Sons Inc., New York, N.Y.

Longhurst; Chapter XV—The Monochromatic Abberratons; Geometrical and Physical Optics—2nd Edition; 1967; pp. 340–355; John Wiley & Sons Inc., New York, N.Y.

Malacara–Doblado; Measuring the curvature of spherical wavefronts with Talbot interferometry; Optical Engineering; vol. 36, No. 7; Jul. 1997; pp. 2016–2024.

Malacara et al.; Null Ronchi Test for Aspherical Surfaces; Applied Optics; Aug. 1974; pp. 1778–1780; vol. 13, No. 8.

Manivannan et al.; Trends in Holographic Recording Materials; Trends in Polymer Science; Aug. 1994; vol. 2, No. 8; pp. 282–290; Elsevier Science Ltd.

Meerholz et al., A photorefractive polymer with high optical gain and diffraction efficiency near 100%, Letters to Nature, Oct. 6, 1994, pp. 497–500, vol. 371.

Mendivil, Intraocular lens implantation through 3.2 versus 4.0 mm incisions; J. Cataract Refract. Surg.; Dec. 1996; pp. 1461–1464; vol. 22: No. 10.

Merker et al.; The Copolymerization of Cyclic Siloxanes, Journal of Polymer Science; 1960; vol. XLIII; pp. 297–310.

Moerner et al., Photorefractive Polymers for Holographic Optical Storage, OSA Technical Digest Series, 1995, pp. 330–333, vol. 21.

Moerner et al.; Polymeric Photorefractive Materials; Chemical Reviews 1994; pp. 127–155; vol. 94; American Chemical Society.

Monroe; Photoinitiators for Free–Radical–Initiated Photoimaging Systems; Chemical Reviews; 1993, vol. 93, No. 1; pp. 435–448; American Chemical Society.

Nakano et al.; Talbot interferometry for measuring the focal length of a lens; Applied Optics; Oct. 1, 1985; pp. 3162–3166; vol. 24, No. 19; Optical Society of America.

Negishi et al., Evaluation of a Zonal–progressive Multifocal Intraocular Lens; American Journal of Ophthalmology; Sep. 1997; pp. 321–330; vol. 124; No. 3; American Journal of Ophthalmology.

Olsen, Sources of error in intraocular lens power calculation; J. Cataract Refract. Surg.; Mar. 1992; pp. 125–129; vol. 18; No. 2.

Olsen et al., Accuracy of the newer generation intraocular lens power calculation formulas in long and short eyes; J. Cataract Refract. Surg.; Mar. 1991; pp. 187–193; vol. 17; No. 2.

Oshika et al., Three year prospective, randomized evaluation of intraocular lens implantation through 3.2 and 5.5 mm incision; J. Cataract Refract Surg.; Apr. 1998; pp. 509–514; vol. 24.

Pierro et al., Clinical Variability in keratometry, ultrasound biometry measurements, and emmetropic intraocular lens power calculation; J. Cataract Refract. Surg.; Jan. 1991; pp. 91–94; vol. 17; No. 1.

Poga et al., High Efficiency Photorefractive Polymer with Immunity to Crystallization, OSA Technical Digest Series, 1995, pp. 342–345, vol. 21.

Pouliquen et al.; Functionalized Polysiloxanes with Thioxanthone Side Groups: A Study of Their Reactivity as Radical Polymerization Macroinitiators: Macromolecules; 1995; pp. 8028–8034; vol. 28; American Chemical Society.

Ravalico et al., Postoperative Cellular Reaction on Various Intraocular Lens Materials; Ophthalmology; Jul. 1997; pp. 1084–1091; vol. 104; No. 7.

Riffle et al.; 2/Elastomeric Polysiloxane Modifiers for Epoxy Networks—Synthesis of Functional Oligomers and Network Formation Studies; Epoxy Resin Chemistry; 1983; pp. 21–54.

Rigbi et al.; Concurrent Chain Extension and Crosslinking of Hydroxyl–Terminated Poly(dimethyl siloxane); Possible Formation of Catenate Structures; Journal of Polymer Science: Polymer Physics Edition; 1986; pp. 443–449; vol. 24, No. 2; John Wiley & Sons, Inc.

Sawhney et al.; Bioerodible Hydrogels Based on Photopolymerized Poly(ethylene glycol)–co–poly(α–hydroxy acid) Diacrylate Macromers; Macromolecules; 1993; pp. 581–587; vol. 26; American Chemical Society.

Smothers et al., Hologram Recording in Dupont's New Photopolymer Materials; IEE Conference Publication; 1989, pp. 184–189; vol. 311.

Smothers et al., Photopolymers for holography; Practical Holography IV; 1990; pp. 20–29; vol. 1212; SPIE.

Steinert et al.; Long–term clinical results of AMO PhacoFlex model SI–18 introcular lens implantation.; J. Cataract Refract. Surg.; May 1995; pp. 331–338; vol. 21; No. 3.

Su et al.; A new technique for measuring the effective focal length of a thick lens or a compound lens; Optics Communications; Aug. 15, 1990; pp. 118–122; vol. 78, No. 2; Elsevier Science Publishers B.V.; North Holland.

Tanabe et al.; Visible Light Photopolymerization: Synthesis of New Fluorone Dyes and Photopolymerization of Acrylic Monomers Using Them; Journal of Polymer Science: Part A: Polymer Chemistry; 1995; pp. 1691–1703; vol. 33; John Wiley & Sons, Inc.

Valdes–Aguilera et al., Photopolymerization Studies Using Visible Light Photoinitiators: Macromolecules; 1992; pp. 541–547; vol. 25, No. 2 ; American Chemical Society.

Yang, Z. et al., Activity and Stability of Enzymes Incorporated into Acrylic Polymers. Journal of American Chemical Society; 1995; pp. 4843–4850; vol. 117; American Chemical Society.

Yilgor et al.; 14/Reactive Difuncitonal Siloxane Oligomers Synthesis and Characterization; American Chemical Society; 1985; pp. 161–174; American Chemical Society.

Yu et al.; Fringe–orientation maps and fringe skeleton extracton by the two–dimensional derivative–sign binary–fringe method; Applied Optics; Oct. 10, 1994; pp. 6873–6878; vol. 33, No. 29: Optical Society of America.

Zhang et al; Photorefractive Polymers and Composites; Advanced Materials; 1996; pp. 111–125; vol. 8, No. 2; VCH Verlagsgesellschaft mbH; Weinheim.

Zobel et al.; A Polysiloxane–Based Photorefractive Polymer with High Optical Gain and Diffraction Efficiency; Advanced Materials; 1995; pp. 911–914; vol. 7, No. 11; VCH Verlagsgesellschaft mbH; Weinheim.

* cited by examiner

LENSES CAPABLE OF POST-FABRICATION POWER MODIFICATION

RELATED APPLICATIONS

This application is a continuation of and claims priority of U.S. application Ser. No. 10/177,722, filed Jun. 18, 2002, which is a continuation of and claims priority of U.S. application Ser. No. 09/416,044, filed Oct. 8, 1999, now U.S. Pat. No. 6,450,642 which claims priority of U.S. Provisional Application No. 60/115,617, filed Jan. 12, 1999; 60/132,871, filed May 5, 1999; and 60/140,298, filed Jun. 17, 1999; and which is fully incorporated herein by reference.

BACKGROUND

Approximately two million cataract surgery procedures are performed in the United States annually. The procedure generally involves making an incision in the anterior lens capsule to remove the cataractous crystalline lens and implanting an intraocular lens in its place. The power of the implanted lens is selected (based upon pre-operative measurements of ocular length and corneal curvature) to enable the patient to see without additional corrective measures (e.g., glasses or contact lenses). Unfortunately, due to errors in measurement, and/or variable lens positioning and wound healing, about half of all patients undergoing this procedure will not enjoy optimal vision without correction after surgery. Brandser et al., *Acta Ophthalmol Scand* 75:162–165 (1997); Oshika et al., *J cataract Refract Surg* 24:509–514 (1998). Because the power of prior art intraocular lenses generally cannot be adjusted once they have been implanted, the patient typically must choose between replacing the implanted lens with another lens of a different power or be resigned to the use of additional corrective lenses such as glasses or contact lenses. Since the benefits typically do not outweigh the risks of the former, it is almost never done.

An intraocular lens whose power may be adjusted after implantation and subsequent wound healing would be an ideal solution to post-operative refractive errors associated with cataract surgery. Moreover, such a lens would have wider applications and may be used to correct more typical conditions such as myopia, hyperopia, and astigmatism. Although surgical procedures such as LASIK which uses a laser to reshape the cornea are available, only low to moderate myopia and hyperopia may be readily treated. In contrast, an intraocular lens, which would function just like glasses or contact lenses to correct for the refractive error of the natural eye, could be implanted in the eye of any patient. Because the power of the implanted lens may be adjusted, post-operative refractive errors due to measurement irregularities and/or variable lens positioning and wound healing may be fine tuned in-situ.

SUMMARY

The present invention relates to optical elements, particularly medical lenses and methods of using the same. In general, the inventive lens comprises (i) a first polymer matrix and (ii) a refraction modulating composition that is capable of stimulus-induced polymerization dispersed therein. In one embodiment, when at least a portion of the lens is exposed to an appropriate stimulus, the refraction modulating composition forms a second polymer matrix, the formation of which modifies lens power.

BRIEF DESCRIPTIONS OF THE DRAWINGS

DETAILED DESCRIPTION OF THE PREFERRED EMBODIMENTS

The present invention relates to optical elements (e.g., lenses and prisms) that are capable of post-fabrication power modifications. More particularly, the present invention relates to intraocular lenses whose power may be adjusted in-situ after implantation in the eye.

The inventive optical elements comprise a first polymer matrix and a refraction modulating composition dispersed therein. The first polymer matrix forms the optical element framework and is generally responsible for many of its material properties. The refraction modulating composition ("RMC") may be a single compound or a combination of compounds that is capable of stimulus-induced polymerization, preferably photo-polymerization. As used herein, the term "polymerization" refers to a reaction wherein at least one of the components of the refraction modulating composition reacts to form at least one covalent or physical bond with either a like component or with a different component. The identities of the first polymer matrix and the refraction modulating compositions will depend on the end use of the optical element. However, as a general rule, the first polymer matrix and the refraction modulating composition are selected such that the components that comprise the refraction modulating composition are capable of diffusion within the first polymer matrix. Put another way, a loose first polymer matrix will tend to be paired with larger RMC components and a tight first polymer matrix will tend to be paired with smaller RMC components.

Figure 1:
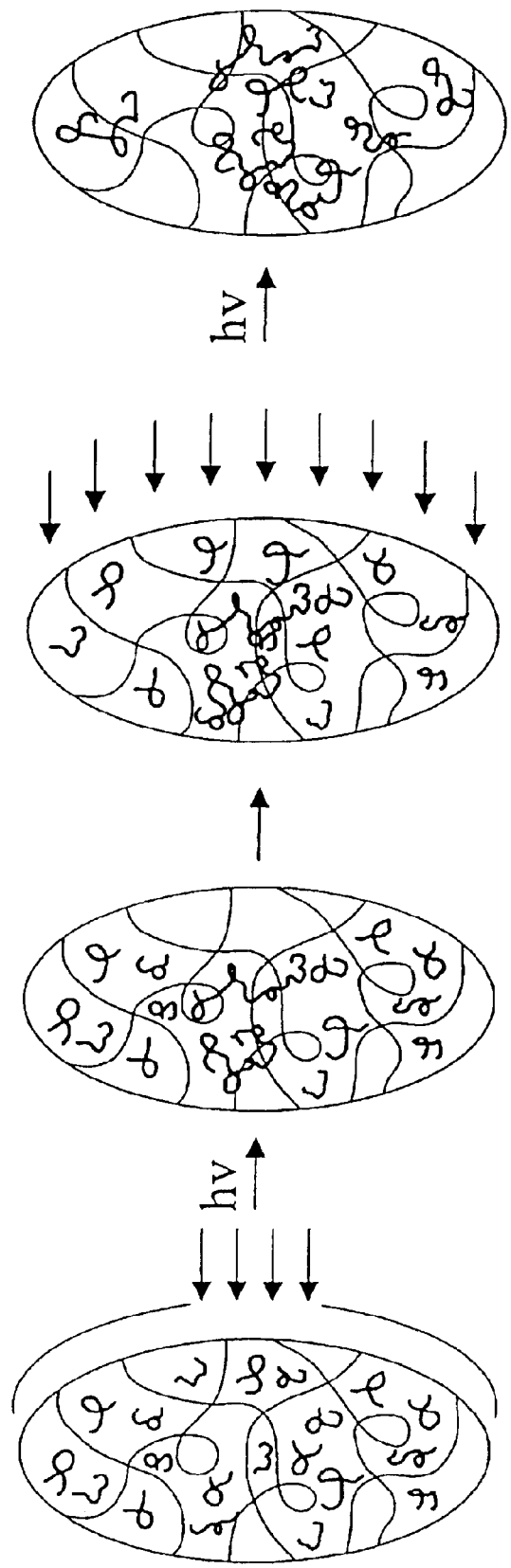
FIG. 1 is a schematic of a lens of the present invention being irradiated in the center followed by irradiation of the entire lens to "lock in" the modified lens power.

Upon exposure to an appropriate energy source (e.g., heat or light), the refraction modulating composition typically forms a second polymer matrix in the exposed region of the optical element. The presence of the second polymer matrix changes the material characteristics of this portion of the optical element to modulate its refraction capabilities. In general, the formation of the second polymer matrix typically increases the refractive index of the affected portion of the optical element. After exposure, the refraction modulating composition in the unexposed region will migrate into the exposed region over time. The amount of RMC migration into the exposed region is time dependent and may be precisely controlled. If enough time is permitted, the RMC components will re-equilibrate and redistribute throughout optical element (i.e., the first polymer matrix, including the exposed region). When the region is re-exposed to the energy source, the refraction modulating composition ("RMC") that has since migrated into the region (which may be less than if the RMC composition were allowed to re-equilibrate) polymerizes to further increase the formation of the second polymer matrix. This process (exposure followed by an appropriate time interval to allow for diffusion) may be repeated until the exposed region of the optical element has reached the desired property (e.g., power, refractive index, or shape). At this point, the entire optical element is exposed to the energy source to "lock-in" the desired lens property by polymerizing the remaining RMC components that are outside the exposed region before the components can migrate into the exposed region. In other words, because freely diffusable RMC components are no longer available, subsequent exposure of the optical element to an energy source cannot further change its power. FIG. 1 illustrates one inventive embodiment, refractive index modulation (thus lens power modulation) followed by a lock in.

The first polymer matrix is a covalently or physically linked structure that functions as an optical element and is formed from a first polymer matrix composition ("FPMC").

In general, the first polymer matrix composition comprises one or more monomers that upon polymerization will form the first polymer matrix. The first polymer matrix composition optionally may include any number of formulation auxiliaries that modulate the polymerization reaction or improve any property of the optical element. Illustrative examples of suitable FPMC monomers include acrylics, methacrylates, phosphazenes, siloxanes, vinyls, homopolymers and copolymers thereof. As used herein, a "monomer" refers to any unit (which may itself either be a homopolymer or copolymer) which may be linked together to form a polymer containing repeating units of the same. If the FPMC monomer is a copolymer, it may be comprised of the same type of monomers (e.g., two different siloxanes) or it may be comprised of different types of monomers (e.g., a siloxane and an acrylic).

In one embodiment, the one or more monomers that form the first polymer matrix are polymerized and cross-linked in the presence of the refraction modulating composition. In another embodiment, polymeric starting material that forms the first polymer matrix is cross-linked in the presence of the refraction modulating composition. Under either scenario, the RMC components must be compatible with and not appreciably interfere with the formation of the first polymer matrix. Similarly, the formation of the second polymer matrix should also be compatible with the existing first polymer matrix. Put another way, the first polymer matrix and the second polymer matrix should not phase separate and light transmission by the optical element should be unaffected.

As described previously, the refraction modulating composition may be a single component or multiple components so long as: (i) it is compatible with the formation of the first polymer matrix; (ii) it remains capable of stimulus-induced polymerization after the formation of the first polymer matrix; and (iii) it is freely diffusable within the first polymer matrix. In preferred embodiments, the stimulus-induced polymerization is photo-induced polymerization.

The inventive optical elements have numerous applications in the electronics and data storage industries. Another application for the present invention is as medical lenses, particularly as intraocular lenses.

In general, there are two types of intraocular lenses ("IOLs"). The first type of an intraocular lens replaces the eye's natural lens. The most common reason for such a procedure is cataracts. The second type of intraocular lens supplements the existing lens and functions as a permanent corrective lens. This type of lens (sometimes referred to as a phakic intraocular lens) is implanted in the anterior or posterior chamber to correct any refractive errors of the eye. In theory, the power for either type of intraocular lenses required for emmetropia (i.e., perfect focus on the retina from light at infinity) can be precisely calculated. However, in practice, due to errors in measurement of corneal curvature, and/or variable lens positioning and wound healing, it is estimated that only about half of all patients undergoing IOL implantation will enjoy the best possible vision without the need for additional correction after surgery. Because prior art IOLs are generally incapable of post-surgical power modification, the remaining patients must resort to other types of vision correction such as external lenses (e.g., glasses or contact lenses) or cornea surgery. The need for these types of additional corrective measures is obviated with the use of the intraocular lenses of the present invention.

The inventive intraocular lens comprises a first polymer matrix and a refraction modulating composition dispersed therein. The first polymer matrix and the refraction modulating composition are as described above with the additional requirement that the resulting lens be biocompatible.

Illustrative examples of a suitable first polymer matrix include: poly-acrylates such as poly-alkyl acrylates and poly-hydroxyalkyl acrylates; poly-methacrylates such as poly-methyl methacrylate ("PMMA"), poly-hydroxyethyl methacrylate ("PHEMA"), and poly-hydroxypropyl methacrylate ("HPMA"); poly-vinyls such as poly-styrene and poly-vinylpyrrolidone ("PNVP"); poly-siloxanes such as poly-dimethylsiloxane; poly-phosphazenes, and copolymers of thereof. U.S. Pat. No. 4,260,725 and patents and references cited therein (which are all incorporated herein by reference) provide more specific examples of suitable polymers that may be used to form the first polymer matrix.

In preferred embodiments, the first polymer matrix generally possesses a relatively low glass transition temperature ("$T_g$") such that the resulting IOL tends to exhibit fluid-like and/or elastomeric behavior, and is typically formed by crosslinking one or more polymeric starting materials wherein each polymeric starting material includes at least one crosslinkable group. Illustrative examples of suitable crosslinkable groups include but are not limited to hydride, acetoxy, alkoxy, amino, anhydride, aryloxy, carboxy, enoxy, epoxy, halide, isocyano, olefinic, and oxime. In more preferred embodiments, each polymeric starting material includes terminal monomers (also referred to as endcaps) that are either the same or different from the one or more monomers that comprise the polymeric starting material but include at least one crosslinkable group. In other words, the terminal monomers begin and end the polymeric starting material and include at least one crosslinkable group as part of its structure. Although it is not necessary for the practice of the present invention, the mechanism for crosslinking the polymeric starting material preferably is different than the mechanism for the stimulus-induced polymerization of the components that comprise the refraction modulating composition. For example, if the refraction modulating composition is polymerized by photo-induced polymerization, then it is preferred that the polymeric starting materials have crosslinkable groups that are polymerized by any mechanism other than photo-induced polymerization.

An especially preferred class of polymeric starting materials for the formation of the first polymer matrix is polysiloxanes (also known as "silicones") endcapped with a terminal monomer which includes a crosslinkable group selected from the group consisting of acetoxy, amino, alkoxy, halide, hydroxy, and mercapto. Because silicone IOLs tend to be flexible and foldable, generally smaller incisions may be used during the IOL implantation procedure. An example of an especially preferred polymeric starting material is bis(diacetoxymethylsilyl)-polydimethylsiloxane (which is polydimethylsiloxane that is endcapped with a diacetoxymethylsilyl terminal monomer).

The refraction modulating composition that is used in fabricating IOLs is as described above except that it has the additional requirement of biocompatibility.

The refraction modulating composition is capable of stimulus-induced polymerization and may be a single component or multiple components so long as: (i) it is compatible with the formation of the first polymer matrix; (ii) it remains capable of stimulus-induced polymerization after the formation of the first polymer matrix; and (iii) it is freely diffusable within the first polymer matrix. In general, the same type of monomers that is used to form the first polymer matrix may be used as a component of the refraction modulating composition. However, because of the requirement that the RMC monomers must be diffusable within the first polymer matrix, the RMC monomers generally tend to be smaller (i.e., have lower molecular weights) than the monomers which form the first polymer matrix. In addition to the one or more monomers, the refraction modulating composition may include other components such as initiators and sensitizers that facilitate the formation of the second polymer matrix.

In preferred embodiments, the stimulus-induced polymerization is photo-polymerization. In other words, the one or more monomers that comprise the refraction modulating composition each preferably includes at least one group that is capable of photopolymerization. Illustrative examples of such photopolymerizable groups include but are not limited to acrylate, allyloxy, cinnamoyl, methacrylate, stibenyl, and vinyl. In more preferred embodiments, the refraction modulating composition includes a photoinitiator (any compound used to generate free radicals) either alone or in the presence of a sensitizer. Examples of suitable photoinitiators include acetophenones (e.g., α-substituted haloacetophenones, and diethoxyacetophenone); 2,4-dichloromethyl-1,3,5-triazines; benzoin methyl ether; and o-benzoyl oximino ketone. Examples of suitable sensitizers include p-(dialkylamino) aryl aldehyde; N-alkylindolylidene; and bis[p-(dialkylamino)benzylidene] ketone.

Because of the preference for flexible and foldable IOLs, an especially preferred class of RMC monomers is polysiloxanes endcapped with a terminal siloxane moiety that includes a photopolymerizable group. An illustrative representation of such a monomer is

X—Y—X¹ wherein Y is a siloxane which may be a monomer, a homopolymer or a copolymer formed from any number of siloxane units, and X and X¹ may be the same or different and are each independently a terminal siloxane moiety that includes a photopolymerizable group. An illustrative example of Y include

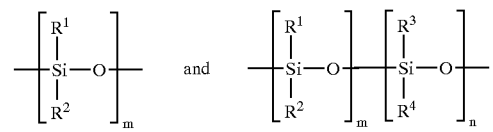

wherein: m and n are independently each an integer and
R¹, R², R³, and R⁴ are independently each hydrogen, alkyl (primary, secondary, tertiary, cyclo), aryl, or heteroaryl. In preferred embodiments, R¹, R², R³, and R⁴ is a $C_1$–$C_{10}$ alkyl or phenyl. Because RMC monomers with a relatively high aryl content have been found to produce larger changes in the refractive index of the inventive lens, it is generally preferred that at least one of R¹, R², R³, and R⁴ is an aryl, particularly phenyl. In more preferred embodiments, R¹, R², and R³ are the same and are methyl, ethyl or propyl and R⁴ is phenyl.

Illustrative examples of X and X¹ (or X¹ and X depending on how the RMC polymer is depicted) are

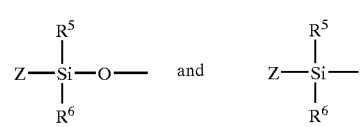

respectively wherein:
R⁵ and R⁶ are independently each hydrogen, alkyl, aryl, or heteroaryl; and
Z is a photopolymerizable group.

In preferred embodiments, R⁵ and R⁶ are independently each a $C_1$–$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, R⁵ and R⁶ is methyl, ethyl, or propyl and Z is a photopolymerizable group that includes an acrylate or methacrylate moiety.

In especially preferred embodiments, an RMC monomer is of the following formula

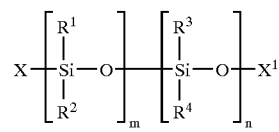

wherein X and X¹ are the same and R¹, R², R³, and R⁴ are as defined previously. Illustrative examples of such RMC monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group.

Although any suitable method may be used, a ring-opening reaction of one or more cyclic siloxanes in the presence of triflic acid has been found to be a particularly efficient method of making one class of inventive RMC monomers. Briefly, the method comprises contacting a cyclic siloxane with a compound of the formula

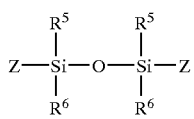

in the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer are contacted with bis-methacryloxypropyltetramethyldisiloxane in the presence of triflic acid to form a dimethyl-siloxane methyl-phenylsiloxane copolymer that is endcapped with a methacryloxylpropyl-dimethylsilane group, an especially preferred RMC monomer.

The inventive IOLs may be fabricated with any suitable method that results in a first polymer matrix with one or more components which comprise the refraction modulating composition dispersed therein, and wherein the refraction modulating composition is capable of stimulus-induced polymerization to form a second polymer matrix. In general, the method for making an inventive IOL is the same as that for making an inventive optical element. In one embodiment, the method comprises mixing a first polymer matrix composition with a refraction modulating composition to form a reaction mixture;

placing the reaction mixture into a mold;

polymerizing the first polymer matrix composition to form said optical element; and, removing the optical element from the mold.

The type of mold that is used will depend on the optical element being made. For example, if the optical element is a prism, then a mold in the shape of a prism is used. Similarly, if the optical element is an intraocular lens, then an intraocular lens mold is used and so forth. As described previously, the first polymer matrix composition comprises one or more monomers for forming the first polymer matrix and optionally includes any number of formulation auxiliaries that either modulate the polymerization reaction or improve any property (whether or not related to the optical characteristic) of the optical element. Similarly, the refraction modulating composition comprises one or more components that together are capable of stimulus-induced polymerization to form the second polymer matrix. Because flexible and foldable intraocular lenses generally permit smaller incisions, it is preferred that both the first polymer matrix composition and the refraction modulating composition include one or more silicone-based or low $T_g$ acrylic monomers when the inventive method is used to make IOLs.

A key advantage of the intraocular lens of the present invention is that an IOL property may be modified after implantation within the eye. For example, any errors in the power calculation due to imperfect corneal measurements and/or variable lens positioning and wound healing may be modified in a post surgical outpatient procedure.

In addition to the change in the IOL refractive index, the stimulus-induced formation of the second polymer matrix has been found to affect the IOL power by altering the lens curvature in a predictable manner. As a result, both mechanisms may be exploited to modulate an IOL property, such as power, after it has been implanted within the eye. In general, the method for implementing an inventive IOL having a first polymer matrix and a refraction modulating composition dispersed therein, comprises:

(a) exposing at least a portion of the lens to a stimulus whereby the stimulus induces the polymerization of the refraction modulating composition.

If after implantation and wound healing, no IOL property needs to be modified, then the exposed portion is the entire lens. The exposure of the entire lens will lock in the then-existing properties of the implanted lens.

However, if a lens characteristic such as its power needs to be modified, then only a portion of the lens (something less than the entire lens) would be exposed. In one embodiment, the method of implementing the inventive IOL further comprises:

(b) waiting an interval of time; and (c) re-exposing the portion of the lens to the stimulus.

This procedure generally will induce the further polymerization of the refraction modulating composition within the exposed lens portion. Steps (b) and (c) may be repeated any number of times until the intraocular lens (or optical element) has reached the desired lens characteristic. At this point, the method may further include the step of exposing the entire lens to the stimulus to lock-in the desired lens property.

In another embodiment wherein a lens property needs to be modified, a method for implementing an inventive IOL comprises:

(a) exposing a first portion of the lens to a stimulus whereby the stimulus induces the polymerization of the refraction modulating composition; and (b) exposing a second portion of the lens to the stimulus.

The first lens portion and the second lens portion represent different regions of the lens although they may overlap. Optionally, the method may include an interval of time between the exposures of the first lens portion and the second lens portion. In addition, the method may further comprise re-exposing the first lens portion and/or the second lens portion any number of times (with or without an interval of time between exposures) or may further comprise exposing additional portions of the lens (e.g., a third lens portion, a fourth lens portion, etc.). Once the desired property has been reached, then the method may further include the step of exposing the entire lens to the stimulus to lock-in the desired lens property.

In general, the location of the one or more exposed portions will vary depending on the type of refractive error being corrected. For example, in one embodiment, the exposed portion of the IOL is the optical zone which is the center region of the lens (e.g., between about 4 mm and about 5 mm in diameter). Alternatively, the one or more exposed lens portions may be along IOL's outer rim or along a particular meridian. In preferred embodiments, the stimulus is light. In more preferred embodiments, the light is from a laser source.

In summary, the present invention relates to a novel optical element that comprises (i) a first polymer matrix and (ii) a refraction modulating composition that is capable of stimulus-induced polymerization dispersed therein. When at least a portion of the optical element is exposed to an appropriate stimulus, the refraction modulating composition forms a second polymer matrix. The amount and location of the second polymer matrix modifies a property such as the power of the optical element by changing its refractive index and/or by altering its shape.

EXAMPLE 1

Materials comprising various amounts of (a) polydimethylsiloxane endcapped with diacetoxymethylsilane ("PDMS") (36000 g/mol), (b) dimethylsiloxane-diphenylsiloxane copolymer endcapped with vinyl-dimethyl silane ("DMDPS") (15,500 g/mol), and (c) a UV-photoinitiator, 2,2-dimethoxy-2-phenylacetophenone ("DMPA") as shown by Table 1 were made and tested. PDMS is the monomer which forms first polymer matrix, and DMDPS and DMPA together comprise the refraction modulating composition.

SCHEME 1

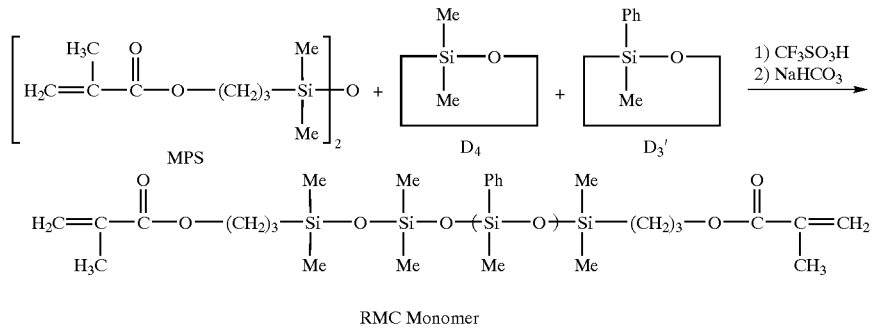

RMC Monomer

TABLE 1

| | PDMS (wt. %) | DMDPS (wt. %) | DMPA (wt %)[a] |
|---|---|---|---|
| 1 | 90 | 10 | 1.5 |
| 2 | 80 | 20 | 1.5 |
| 3 | 75 | 25 | 1.5 |
| 4 | 70 | 30 | 1.5 |

[a]wt % with respect to DMDPS.

Briefly, appropriate amounts of PMDS (Gelest DMS-D33; 36000 g/mol), DMDPS (Gelest PDV-0325; 3.0–3.5 mole % diphenyl, 15,500 g/mol), and DMPA (Acros; 1.5 wt % with respect to DMDPS) were weighed together in an aluminum pan, manually mixed at room temperature until the DMPA dissolved, and degassed under pressure (5 mtorr) for 2–4 minutes to remove air bubbles. Photosensitive prisms were fabricated by pouring the resulting silicone composition into a mold made of three glass slides held together by scotch tape in the form of a prism and sealed at one end with silicone caulk. The prisms are ~5 cm long and the dimensions of the three sides are ~8 mm each. The PDMS in the prisms was moisture cured and stored in the dark at room temperature for a period of 7 days to ensure that the resulting first polymer matrix was non-tacky, clear, and transparent.

The amount of photoinitiator (1.5 wt. %) was based on prior experiments with fixed RMC monomer content of 25% in which the photoinitiator content was varied. Maximal refractive index modulation was observed for compositions containing 1.5% and 2 wt. % photoinitiator while saturation in refractive index occurred at 5 wt. %.

EXAMPLE 2
Synthesis RMC Monomers

As illustrated by Scheme 1, commercially available cyclic dimethylsiloxane tetramer ("$D_4$"), cyclic methylphenylsiloxane trimer ("$D_3$'") in various ratios were ring-opened by triflic acid and bis-methacryloxylpropyltetramethyldisiloxane ("MPS") were reacted in a one pot synthesis. U.S. Pat. No. 4,260,725; Kunzler, J. F., Trends in Polymer Science, 4: 52–59 (1996); Kunzler et al. J. Appl. Poly. Sci., 55: 611–619 (1995); and Lai et al., J. Poly. Sci. A. Poly. Chem., 33: 1773–1782 (1995).

Briefly, appropriate amounts of MPS, $D_4$, and $D_3$' were stirred in a vial for 1.5–2 hours. An appropriate amount of triflic acid was added and the resulting mixture was stirred for another 20 hours at room temperature. The reaction mixture was diluted with hexane, neutralized (the acid) by the addition of sodium bicarbonate, and dried by the addition of anhydrous sodium sulfate. After filtration and rotovaporation of hexane, the RMC monomer was purified by further filtration through an activated carbon column. The RMC monomer was dried at 5 mtorr of pressure between 70–80° C. for 12–18 hours.

The amounts of phenyl, methyl, and endgroup incorporation were calculated from $^1$H-NMR spectra that were run in deuterated chloroform without internal standard tetramethylsilane ("TMS"). Illustrative examples of chemical shifts for some of the synthesized RMC monomers follows. A 1000 g/mole RMC monomer containing 5.58 mole % phenyl (made by reacting: 4.85 g (12.5 mmole) of MPS; 1.68 g (4.1 mmole) of $D_3$'; 5.98 g (20.2 mmole) of $D_4$; and 108 μl (1.21 mmole) of triflic acid: δ=7.56–7.57 ppm (m, 2H) aromatic, δ=7.32–7.33 ppm (m, 3H) aromatic, δ=6.09 ppm (d, 2H) olefinic, δ=5.53 ppm (d, 2H) olefinic, δ=4.07–4.10 ppm (t, 4H) —O—C$\underline{H}_2$CH$_2$CH$_2$—, δ=1.93 ppm (s, 6H) methyl of methacrylate, δ=1.65–1.71 ppm (m, 4H) —O—CH$_2$C$\underline{H}_2$CH$_2$—, δ=0.54–0.58 ppm (m, 4H) —O—CH$_2$CH$_2$C$\underline{H}_2$—Si, δ=0.29–0.30 ppm (d, 3H) C$\underline{H}_3$—Si-Phenyl, δ=0.04–0.08 ppm (s, 50 H) (C$\underline{H}_3$)$_2$Si of the backbone.

A 2000 g/mole RMC monomer containing 5.26 mole % phenyl (made by reacting: 2.32 g (6.0 mmole) of MPS; 1.94 g (4.7 mmole) of $D_3$'; 7.74 g (26.1 mmole) of $D_4$; and 136 μl (1.54 mmole) of triflic acid: δ=7.54–7.58 ppm (m, 4H) aromatic, δ=7.32–7.34 ppm (m, 6H) aromatic, δ=6.09 ppm (d, 2H) olefinic, δ=5.53 ppm (d, 2H) olefinic, δ=4.08–4.11 ppm (t, 4H) —O—C$\underline{H}_2$CH$_2$CH$_2$—, δ=1.94 ppm (s, 6H) methyl of methacrylate, δ=1.67–1.71 ppm (m, 4H) —O—CH$_2$C$\underline{H}_2$CH$_2$—, δ=0.54–0.59 ppm (m, 4H) —O—CH$_2$CH$_2$C$\underline{H}_2$—Si, δ=0.29–0.31 ppm (s, 6H), C$\underline{H}_3$—Si-Phenyl, δ=0.04–0.09 ppm (s, 112H) (C$\underline{H}_3$)$_2$Si of the backbone.

A 4000 g/mole RMC monomer containing 4.16 mole % phenyl (made by reacting: 1.06 g (2.74 mmole) of MPS; 1.67 g (4.1 mmole) of $D_3$'; 9.28 g (31.3 mmole) of $D_4$; and 157 μl (1.77 mmole) of triflic acid: δ=7.57–7.60 ppm (m, 8H) aromatic, δ=7.32–7.34 ppm (m, 12H) aromatic, δ=6.10 ppm (d, 2H) olefinic, δ=5.54 ppm (d, 2H) olefinic, δ=4.08–4.12 ppm (t, 4H) —O—C$\underline{H}_2$CH$_2$CH$_2$—, δ=1.94 ppm (s, 6H) methyl of methacrylate, δ=1.65–1.74 ppm (m, 4H) —O—CH$_2$C$\underline{H}_2$CH$_2$—, δ=0.55–0.59 ppm (m, 4H) —O—CH$_2$CH$_2$C$\underline{H}_2$—Si, δ=0.31 ppm (m, 11H), C$\underline{H}_3$—Si-Phenyl, δ=0.07–0.09 ppm (s, 272 H) (C$\underline{H}_3$)$_2$Si of the backbone.

Similarly, to synthesize dimethylsiloxane polymer without any methylphenylsiloxane units and endcapped with methyacryloxypropyl dimethylsilane, the ratio of D$_4$ to MPS was varied without incorporating D'$_3$.

Molecular weights were calculated by $^1$H-NMR and by gel permeation chromatography ("GPC"). Absolute molecular weights were obtained by universal calibration method using polystyrene and poly(methyl methacrylate) standards. Table 2 shows the characterization of other RMC monomers synthesized by the triflic acid ring opening polymerization.

TABLE 2

| | Mole % Phenyl | Mole % Methyl | Mole % Methacrylate | Mn (NMR) | Mn (GPC) | n$_D$ |
|---|---|---|---|---|---|---|
| A | 6.17 | 87.5 | 6.32 | 1001 | 946 | 1.44061 |
| B | 3.04 | 90.8 | 6.16 | 985 | 716 | 1.43188 |
| C | 5.26 | 92.1 | 2.62 | 1906 | 1880 | — |
| D | 4.16 | 94.8 | 1.06 | 4054 | 4200 | 1.42427 |
| E | 0 | 94.17 | 5.83 | 987 | 1020 | 1.42272 |
| F | 0 | 98.88 | 1.12 | 3661 | 4300 | 1.40843 |

At 10–40 wt %, these RMC monomers of molecular weights 1000 to 4000 g/mol with 3–6.2 mole % phenyl content are completely miscible, biocompatible, and form optically clear prisms and lenses when incorporated in the silicone matrix. RMC monomers with high phenyl content (4–6 mole %) and low molecular weight (1000–4000 g/mol) resulted in increases in refractive index change of 2.5 times and increases in speeds of diffusion of 3.5 to 5.0 times compared to the RMC monomer used in Table 1 (dimethylsiloxane-diphenylsiloxane copolymer endcapped with vinyldimethyl silane ("DMDPS") (3–3.5 mole % diphenyl content, 15500 g/mol). These RMC monomers were used to make optical elements comprising: (a) polydimethylsiloxane endcapped with diacetoxymethylsilane ("PDMS") (36000 g/mol), (b) dimethylsiloxane methylphenylsiloxane copolymer that is endcapped with a methacryloxylpropyldimethylsilane group, and (c) 2,2-dimethoxy-2-phenylacetophenone ("DMPA"). Note that component (a) is the monomer that forms the first polymer matrix and components (b) and (c) comprise the refraction modulating composition.

EXAMPLE 3

Fabrication of Intraocular Lenses ("IOL")

An intraocular mold was designed according to well-accepted standards. See e.g., U.S. Pat. Nos. 5,762,836; 5,141,678; and 5,213,825. Briefly, the mold is built around two plano-concave surfaces possessing radii of curvatures of −6.46 mm and/or −12.92 mm, respectively. The resulting lenses are 6.35 mm in diameter and possess a thickness ranging from 0.64 mm, 0.98 mm, or 1.32 mm depending upon the combination of concave lens surfaces used. Using two different radii of curvatures in their three possible combinations and assuming a nominal refractive index of 1.404 for the IOL composition, lenses with pre-irradiation powers of 10.51 D (62.09 D in air), 15.75 D (92.44 in air), and 20.95 D (121.46 D in air) were fabricated.

EXAMPLE 4

Stability of Compositions against Leaching

Three IOLs were fabricated with 30 and 10 wt % of RMC monomers B and D incorporated in 60 wt % of the PDMS matrix. After moisture curing of PDMS to form the first polymer matrix, the presence of any free RMC monomer in the aqueous solution was analyzed as follows. Two out of three lenses were irradiated three times for a period of 2 minutes using 340 nm light, while the third was not irradiated at all. One of the irradiated lenses was then locked by exposing the entire lens matrix to radiation. All three lenses were mechanically shaken for 3 days in 1.0 M NaCl solution. The NaCl solutions were then extracted by hexane and analyzed by $^1$H-NMR. No peaks due to the RMC monomer were observed in the NMR spectrum. These results suggest that the RMC monomers did not leach out of the matrix into the aqueous phase in all three cases. Earlier studies on a vinyl endcapped silicone RMC monomer showed similar results even after being stored in 1.0 M NaCl solution for more than one year.

EXAMPLE 5

Toxicological Studies in Rabbit Eyes

Sterilized, unirradiated and irradiated silicone IOLs (fabricated as described in Example 3) of the present invention and a sterilized commercially available silicone IOL were implanted in albino rabbit eyes. After clinically following the eyes for one week, the rabbits were sacrificed. The extracted eyes were enucleated, placed in formalin and studied histopathologically. There is no evidence of corneal toxicity, anterior segment inflammation, or other signs of lens toxicity.

EXAMPLE 6

Irradiation of Silicone Prisms

Because of the ease of measuring refractive index change (Δn) and percent net refractive index change (% Δn) of prisms, the inventive formulations were molded into prisms for irradiation and characterization. Prisms were fabricated by mixing and pouring (a) 90–60 wt % of high M$_n$ PDMS, (b) 10–40 wt % of RMC monomers in Table 2, and (c) 0.75 wt % (with respect to the RMC monomers) of the photoinitiator DMPA into glass molds in the form of prisms 5 cm long and 8.0 mm on each side. The silicone composition in the prisms was moisture cured and stored in the dark at room temperature for a period of 7 days to ensure that the final matrix was non-tacky, clear and transparent.

Figure 2:
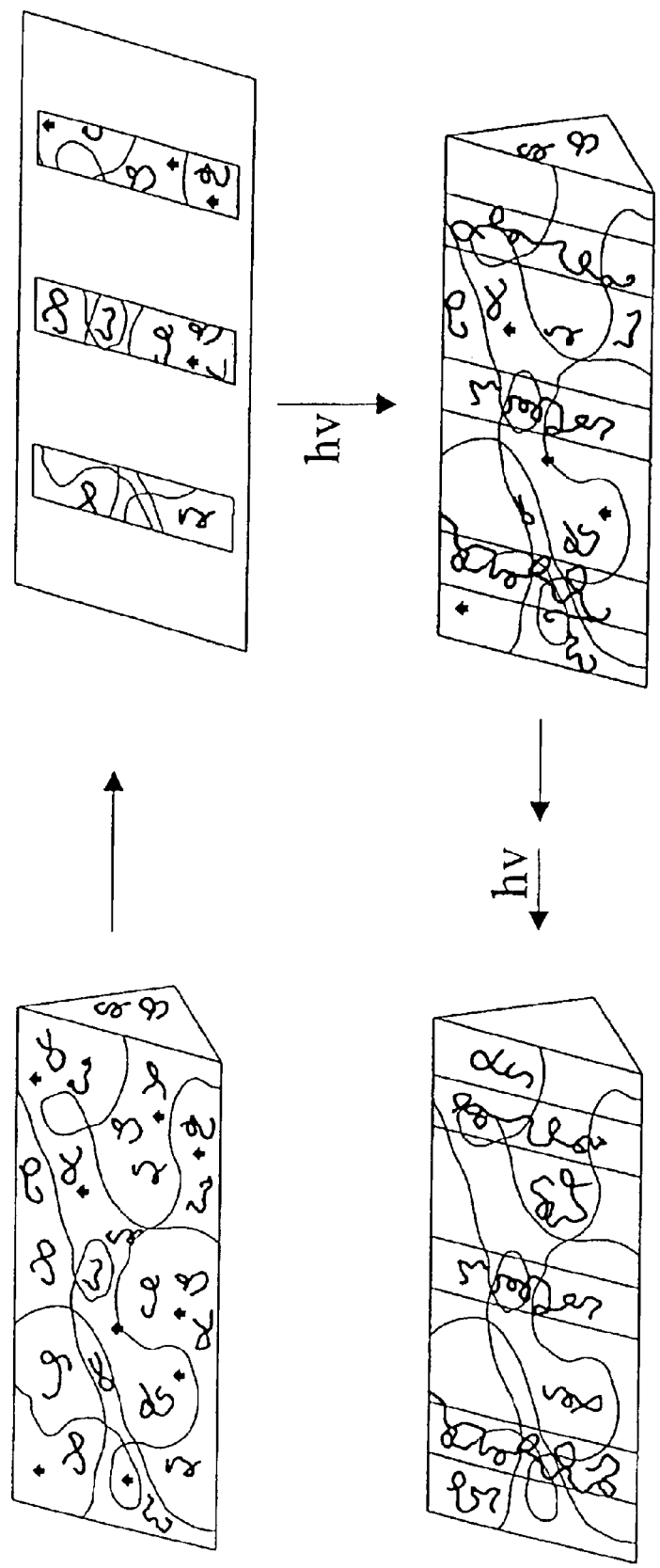
FIG. 2 illustrates the prism irradiation procedure that is used to quantify the refractive index changes after being exposed to various amounts of irradiation.

Two of the long sides of each prism were covered by a black background while the third was covered by a photomask made of an aluminum plate with rectangular windows (2.5 mm×10 mm). Each prism was exposed to a flux of 1.2 mW/cm$^2$ of a collimated 340 nm light (peak absorption of the photoinitiator) from a 1000 W Xe:Hg arc lamp for various time periods. The ANSI guidelines indicate that the maximum permissible exposure ("MPE") at the retina using 340 nm light for a 10–30000 s exposure is 1000 mJ/cm$^2$. Criteria for Exposure of Eye and Skin. *American National Standard* Z136.1: 31–42 (1993). The single dose intensity 1.2 mW/cm$^2$ of 340 nm light for a period of 2 minutes corresponds to 144 mJ/cm$^2$ which is well within the ANSI guidelines. In fact, even the overall intensity for three exposures (432 mJ/cm$^2$) is well within the ANSI guidelines. FIG. 2 is an illustration of the prism irradiation procedure.

The prisms were subject to both (i) continuous irradiation—one-time exposure for a known time period, and (ii) "staccato" irradiation—three shorter exposures with long intervals between them. During continuous irradiation, the refractive index contrast is dependent on the crosslinking density and the mole % phenyl groups, while in the interrupted irradiation, RMC monomer diffusion and further crosslinking also play an important role. During staccato irradiation, the RMC monomer polymerization depends on the rate of propagation during each exposure and the extent of interdiffusion of free RMC monomer during the intervals between exposures. Typical values for the diffusion coefficient of oligomers (similar to the 1000 g/mole RMC monomers used in the practice of the present invention) in a silicone matrix are on the order of $10^{-6}$ to $10^{-7}$ cm$^2$/s. In other words, the inventive RMC monomers require approximately 2.8 to 28 hours to diffuse 1 mm (roughly the half width of the irradiated bands). The distance of a typical optical zone in an IOL is about 4 to about 5 mm across. However, the distance of the optical zone may also be outside of this range. After the appropriate exposures, the prisms were irradiated without the photomask (thus exposing the entire matrix) for 6 minutes using a medium pressure mercury-arc lamp. This polymerized the remaining silicone RMC monomers and thus "locked" the refractive index of the prism in place. Notably, the combined total irradiation of the localized exposures and the "lock-in" exposure was still within ANSI guidelines.

EXAMPLE 7
Prism Dose Response Curves

Inventive prisms fabricated from RMC monomers described by Table 2 were masked and initially exposed for 0.5, 1, 2, 5, and 10 minutes using 1.2 mW/cm$^2$ of the 340 nm line from a 1000 W Xe:Hg arc lamp. The exposed regions of the prisms were marked, the mask detached and the refractive index changes measured. The refractive index modulation of the prisms was measured by observing the deflection of a sheet of laser light passed through the prism. The difference in deflection of the beam passing through the exposed and unexposed regions was used to quantify the refractive index change ($\Delta$n) and the percentage change in the refractive index (% $\Delta$n).

After three hours, the prisms were remasked with the windows overlapping with the previously exposed regions and irradiated for a second time for 0.5, 1, 2, and 5 minutes (total time thus equaled 1, 2, 4, and 10 minutes respectively). The masks were detached and the refractive index changes measured. After another three hours, the prisms were exposed a third time for 0.5, 1, and 2 minutes (total time thus equaled 1.5, 3, and 6 minutes) and the refractive index changes ere measured. As expected, the % $\Delta$n increased with exposure time for each prism after each exposure resulting in prototypical dose response curves. Based upon these results, adequate RMC monomer diffusion appears to occur in about 3 hours for 1000 g/mole RMC monomer.

All of the RMC monomers (B-F) except for RMC monomer A resulted in optically clear and transparent prisms before and after their respective exposures. For example, the largest % $\Delta$n for RMC monomers B, C, and D at 40 wt % incorporation into 60 wt % FPMC were 0.52%, 0.63% and 0.30% respectively which corresponded to 6 minutes of total exposure (three exposures of 2 minutes each separated by 3 hour intervals for RMC monomer B and 3 days for RMC monomers C and D). However, although it produced the largest change in refractive index (0.95%), the prism fabricated from RMC monomer A (also at 40 wt % incorporatioin into 60 wt % FPMC and 6 minutes of total exposure—three exposures of 2 minutes each separated by 3 hour intervals) turned somewhat cloudy. Thus, if RMC monomer A were used to fabricate an IOL, then the RMC must include less than 40 wt % of RMC monomer A or the % $\Delta$n must be kept below the point where the optical clarity of the material is compromised.

A comparison between the continuous and staccato irradiation for RMC A and C in the prisms shows that lower % $\Delta$n values occurs in prisms exposed to continuous irradiation as compared to those observed using staccato irradiations. As indicated by these results, the time interval between exposures (which is related to the amount of RMC diffusion from the unexposed to exposed regions) may be exploited to precisely modulate the refractive index of any material made from the inventive polymer compositions.

Exposure of the entire, previously irradiated prisms to a medium pressure Hg arc lamp polymerized any remaining free RMC, effectively locking the refractive index contrast. Measurement of the refractive index change before and after photolocking indicated no further modulation in the refractive index.

EXAMPLE 8
Optical Characterization of IOLs

Talbot interferometry and the Ronchi test were used to qualitatively and quantitatively measure any primary optical aberrations (primary spherical, coma, astigmatism, field curvature, and distortion) present in pre- and post-irradiated lenses as well as quantifying changes in power upon photopolymerization.

In Talbot interferometry, the test IOL is positioned between the two Ronchi rulings with the second grating placed outside the focus of the IOL and rotated at a known angle, $\theta$, with respect to the first grating. Superposition of the autoimage of the first Ronchi ruling ($p_1$=300 lines/inch) onto the second grating ($P_2$=150 lines/inch) produces moiré fringes inclined at an angle, $\alpha_1$. A second moiré fringe pattern is constructed by axial displacement of the second Ronchi ruling along the optic axis a known distance, d, from the test lens. Displacement of the second grating allows the autoimage of the first Ronchi ruling to increase in magnification causing the observed moiré fringe pattern to rotate to a new angle, $\alpha_2$. Knowledge of moiré pitch angles permits determination of the focal length of the lens (or inversely its power) through the expression:

$$f = \frac{P_1}{P_2} d \left( \frac{1}{\tan\alpha_2 \sin\theta + \cos\theta} - \frac{1}{\tan\alpha_1 \sin\theta + \cos\theta} \right)^{-1}$$

Figure 3:
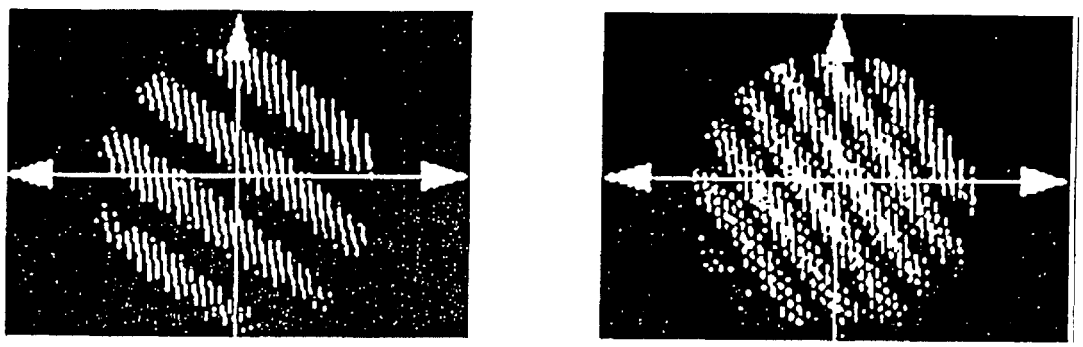
FIG. 3 shows unfiltered moiré fringe patterns of an inventive IOL. The angle between the two Ronchi rulings was set at 12° and the displacement distance between the first and second moiré patterns was 4.92 mm.

To illustrate the applicability of Talbot interferometry to this work, moiré fringe patterns of one of the inventive, pre-irradiated IOLs (60 wt % PDMS, 30 wt % RMC monomer B, 10 wt % RMC monomer D, and 0.75% DMPA relative to the two RMC monomers) measured in air is presented in FIG. 3. Each of the moiré fringes was fitted with a least squares fitting algorithm specifically designed for the processing of moiré patterns. The angle between the two Ronchi rulings was set at 12°, the displacement between the second Ronchi ruling between the first and second moiré fringe patterns was 4.92 mm, and the pitch angles of the moiré fringes, measured relative to an orthogonal coordinate system defined by the optic axis of the instrument and crossing the two Ronchi rulings at 90°, were $\alpha_1$=−33.2°±0.30° and $\alpha_2$=−52.7°±0.40°. Substitution of these values into the above equation results in a focal length of 10.71±0.50 mm (power=93.77±4.6 D).

Figure 4:
FIG. 4 is a Ronchigram of an inventive IOL. The Ronchi pattern corresponds to a 2.6 mm central region of the lens.

Optical aberrations of the inventive IOLs (from either fabrication or from the stimulus-induced polymerization of the RMC components) were monitored using the "Ronchi Test" which involves removing the second Ronchi ruling from the Talbot interferometer and observing the magnified autoimage of the first Ronchi ruling after passage though the test IOL. The aberrations of the test lens manifest themselves by the geometric distortion of the fringe system (produced by the Ronchi ruling) when viewed in the image plane. A knowledge of the distorted image reveals the aberration of the lens. In general, the inventive fabricated lenses (both pre and post irradiation treatments) exhibited sharp, parallel, periodic spacing of the interference fringes indicating an absence of the majority of primary-order optical aberrations, high optical surface quality, homogeneity of n in the bulk, and constant lens power. FIG. 4 is an illustrative example of a Ronchigram of an inventive, pre-irradiated IOL that was fabricated from 60 wt % PDMS, 30 wt % RMC monomer B, 10 wt % RMC monomer D, and 0.75% of DMPA relative to the 2 RMC monomers.

The use of a single Ronchi ruling may also be used to measure the degree of convergence of a refracted wavefront (i.e., the power). In this measurement, the test IOL is placed in contact with the first Ronchi ruling, collimated light is brought incident upon the Ronchi ruling, and the lens and the magnified autoimage is projected onto an observation screen. Magnification of the autoimage enables measurement of the curvature of the refracted wavefront by measuring the spatial frequency of the projected fringe pattern. These statements are quantified by the following equation:

$$P_v = \frac{1000}{L}\left(1 + \frac{d_s}{d}\right)$$

wherein $P_v$ is the power of the lens expressed in diopters, L is the distance from the lens to the observing plane, $d_s$, is the magnified fringe spacing of the first Ronchi ruling, and d is the original grating spacing.

EXAMPLE 9
Power Changes from Photopolymerization of the Inventive IOLs

An inventive IOL was fabricated as described by Example 3 comprising 60 wt % PDMS ($n_D$=1.404), 30 wt % of RMC monomer B ($n_D$=1.4319) 10 wt % of RMC monomer D ($n_D$=1.4243), and 0.75 wt % of the photoinitiator DMPA relative to the combined weight percents of the two RMC monomers. The IOL was fitted with a 1 mm diameter photomask and exposed to 1.2 mW/cm$^2$ of 340 nm collimated light from a 1000 W Xe:Hg arc lamp for two minutes. The irradiated lens was then placed in the dark for three hours to permit polymerization and RMC monomer diffusion. The IOL was photolocked by continuously exposing the entire for six minutes using the aforementioned light conditions. Measurement of the moiré pitch angles followed by substitution into equation 1 resulted in a power of 95.1±2.9 D (f=10.52±0.32 mm) and 104.1±3.6 D (f=9.61 mm±0.32 mm) for the unirradiated and irradiated zones, respectively.

The magnitude of the power increase was more than what was predicted from the prism experiments where a 0.6% increase in the refractive index was routinely achieved. If a similar increase in the refractive index was achieved in the IOL, then the expected change in the refractive index would be 1.4144 to 1.4229. Using the new refractive index (1.4229) in the calculation of the lens power (in air) and assuming the dimensions of the lens did not change upon photopolymerization, a lens power of 96.71 D (f=10.34 mm) was calculated. Since this value is less than the observed power of 104.1±3.6 D, the additional increase in power must be from another mechanism.

Figure 5:
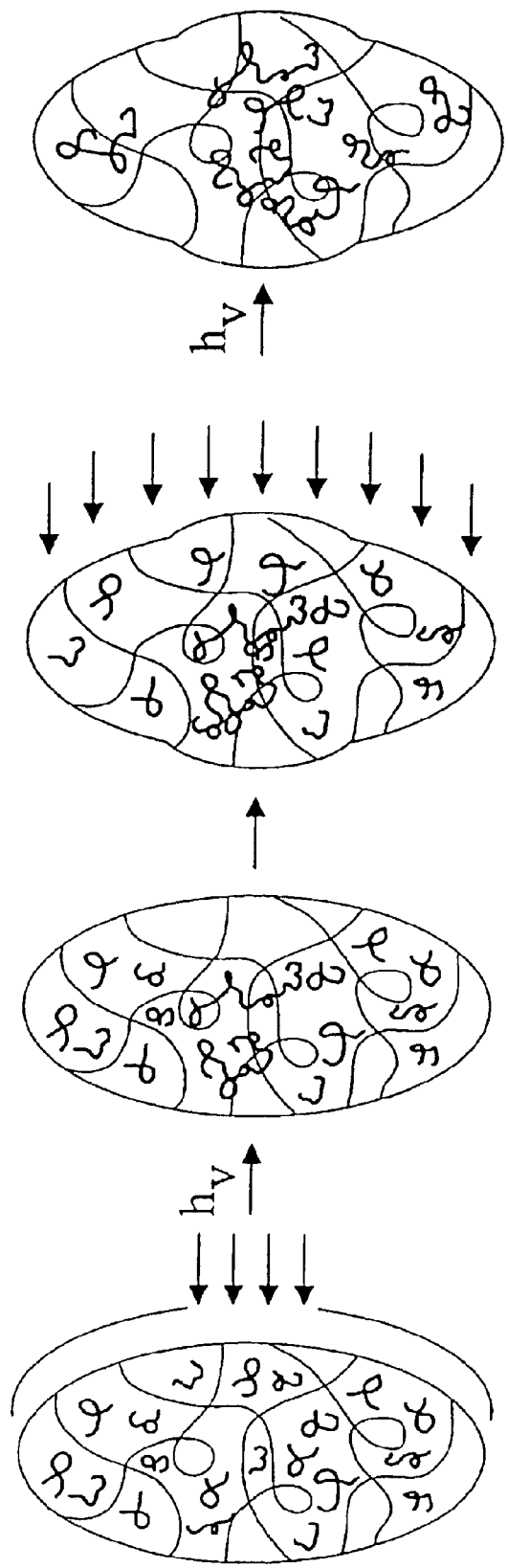
FIG. 5 is a schematic illustrating a second mechanism whereby the formation of the second polymer matrix modulates a lens property by altering lens shape.

Further study of the photopolymerized IOL showed that subsequent RMC monomer diffusion after the initial radiation exposure leads to changes in the radius of curvature of the lens. See e.g., FIG. 5. The RMC monomer migration from the unradiated zone into the radiated zone causes either or both of anterior and posterior surfaces of the lens to swell thus changing the radius of curvature of the lens. It has been determined that a 7% decrease in the radius of curvature for both surfaces is sufficient to explain the observed increase in lens power.

Figure 6:
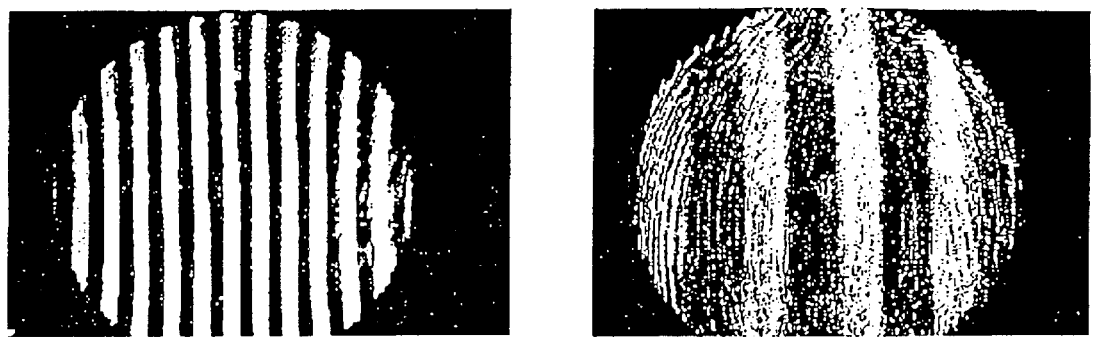
FIG. 6 are Ronchi interferograms of an IOL before and after laser treatment depicting approximately a +8.6 diopter change in lens power within the eye. The spacing of alternative light and dark bands is proportional to lens power.

The concomitant change in the radius of curvature was further studied. An identical IOL described above was fabricated. A Ronchi interferogram of the IOL is shown in FIG. 6a (left interferogram). Using a Talbot interferometer, the focal length of the lens was experimentally determined to be 10.52±0.30 mm (95.1 D±2.8 D). The IOL was then fitted with a 1 mm photomask and irradiated with 1.2 mW/cm$^2$ of 340 collimated light from a 1000 W Xe:Hg arc lamp continuously for 2.5 minutes. Unlike the previous IOL, this lens was not "locked in" three hours after irradiation. FIG. 6b (right interferogram) is the Ronchi interferogram of the lens taken six days after irradiation. The most obvious feature between the two interference patterns is the dramatic increase in the fringe spacing, which is indicative of an increase in the refractive power of the lens.

Measurement of the fringe spacings indicates an increase of approximately +38 diopters in air (f≈7.5 mm). This corresponds to a change in the order of approximately +8.6 diopters in the eye. Since most post-operative corrections from cataract surgery are within 2 diopters, this experiment indicates that the use of the inventive IOLS will permit a relatively large therapeutic window.

EXAMPLE 10
Photopolymerization Studies of Non-phenyl-containing IOLs

Inventive IOLs containing non-phenyl containing RMC monomers were fabricated to further study the swelling from the formation of the second polymer matrix. An illustrative example of such an IOL was fabricated from 60 wt % PDMS, 30 wt % RMC monomer E, 10 wt % RMC monomer F, and 0.75% DMPA relative to the two RMC monomers. The pre-irradiation focal length of the resulting IOL was 10.76 mm (92.94±2.21 D).

In this experiment, the light source was a 325 nm laser line from a He:Cd laser. A 1 mm diameter photomask was placed over the lens and exposed to a collimated flux of 0.75 mW/cm$^2$ at 325 nm for a period of two minutes. The lens was then placed in the dark for three hours. Experimental measurements indicated that the focal length of the IOL changed from 10.76 mm±0.25 mm (92.94 D±2.21 D) to 8.07 mm±0.74 mm (123.92 D±10.59 D) or a dioptric change of +30.98 D±10.82 D in air. This corresponds to an approximate change of +6.68 D in the eye. The amount of irradiation required to induce these changes is only 0.09 J/cm$^2$, a value well under the ANSI maximum permissible exposure ("MPE") level of 1.0 J/cm$^2$.

EXAMPLE 11
Monitoring for Potential IOL Changes from Ambient Light

The optical power and quality of the inventive IOLs were monitored to show that handling and ambient light conditions do not produce any unwanted changes in lens power. A 1 mm open diameter photomask was placed over the central region of an inventive IOL (containing 60 wt % PDMS, 30 wt % RMC monomer E, 10 wt % RMC momnomer F, and 0.75 wt % DMPA relative to the two RMC monomers), exposed to continuous room light for a period of 96 hours, and the spatial frequency of the Ronchi patterns as well as the moiré fringe angles were monitored every 24 hours. Using the method of moiré fringes, the focal length measured in the air of the lens immediately after removal from the lens mold is 10.87±0.23 mm (92.00 D±1.98 D) and after 96 hours apf exposure to ambient room light is 10.74 mm±0.25 mm (93.11 D±2.22 D). Thus, within the experimental uncertainty of the measurement, it is shown that ambient light does not induce any unwanted change in power. A comparison of the resulting Ronchi patterns showed no change in spatial frequency or quality of the interference pattern, confirming that exposure to room light does not affect the power or quality of the inventive IOLs.

EXAMPLE 12
Effect of the Lock in Procedure of an Irradiated IOL

An inventive IOL whose power had been modulated by irradiation was tested to see if the lock-in procedure resulted in further modification of lens power. An IOL fabricated from 60 wt % PDMS, 30 wt % RMC monomer E, 10 wt % RMC monomer F, and 0.75% DMPA relative to the two RMC monomers was irradiated for two minutes with 0.75 mW/cm² of the 325 nm laser line from a He:Cd laser and was exposed for eight minutes to a medium pressure Hg arc lamp. Comparisons of the Talbot images before and after the lock in procedure showed that the lens power remained unchanged. The sharp contrast of the interference fringes indicated that the optical quality of the inventive lens also remained unaffected.

To determine if the lock-procedure was complete, the IOL was refitted with a 1 mm diameter photomask and exposed a second time to 0.75 mW/cm² of the 325 laser line for two minutes. As before, no observable change in fringe space or in optical quality of the lens was observed.

EXAMPLE 13
Monitoring for Potential IOL Changes from the Lock-in

A situation may arise wherein the implanted IOL does not require post-operative power modification, in such cases, the IOL must be locked in so that its characteristic will not be subject to change. To determine if the lock-in procedure induces undesired changes in the refractive power of a previously unirradiated IOL, the inventive IOL (containing 60 wt % PDMS, 30 wt % RMC monomer E, 10 wt % RMC monomer F, and 0.75 wt % DMPA relative to the two RMC monomers) was subject to three 2 minute irradiations over its entire area that was separated by a 3 hour interval using 0.75 mW/cm² of the 325 laser line from a He:Cd laser. Ronchigrams and moiré fringe patterns were taken prior to and after each subsequent irradiation. The moiré fringe patterns taken of the inventive IOL in air immediately after removal from the lens mold and after the third 2 minute irradiation indicate a focal length of 10.50 mm±0.39 mm (95.24 D±3.69 D) and 10.12 mm±0.39 mm (93.28 D±3.53D) respectively. These measurements indicate that photolocking a previously unexposed lens does not induce unwanted changes in power. In addition, no discernable change in fringe spacing or quality of the Ronchi fringes was detected indicating that the refractive power had not changed due to the lock-in.

What is claimed is:

1. A method for implementing an optical element comprising:
   (a) providing an optical element having a refraction modulating composition dispersed therein, wherein the refraction modulating composition is capable of stimulus induced polymerization;
   (b) exposing at least a portion of the element to stimulus;
   (c) waiting an interval of time; and
   (d) exposing at least a portion of the element to stimulus.

2. The method of claims 1 wherein the portion of the element exposed in step (d) is the same portion exposed in step (b).

3. The method of claim 1 wherein the portion of the element exposed in step (d) is the entire element.

4. The method of claim 1 wherein the external stimulus is light.

5. The method of claim 1, wherein the external stimulus is ultraviolet light.

6. The method of claim 1 wherein the exposure step of exposing at least a portion of the lens to an external stimulus (C) causes a change in the optical properties of the lens.

7. The method of claim 6 wherein the change in optical properties is induced by the stimulus induced polymerization of the refraction modulating composition.

8. The method of claim 1 wherein the step of exposing the same or different portion of the lens to an external stimulus (d) causes further changes to the optical properties of the lens.

9. The method of claim 8 wherein the change in optical properties is induced by the stimulus induced polymerization of the refraction modulating composition.

10. The method of claim 1 further comprising the step of repeating steps (b) through (d).

11. The method of claim 1, wherein the refraction modulating composition is capable of photo-induced polymerization.

12. The method of claim 1 wherein the interval of time is determined by the diffusion rate of the refraction modulating composition.

13. The method of claim 1 wherein the intraocular lens further comprises a first polymer matrix.

14. The method of claim 13 wherein the first polymer matrix is selected from the group consisting of polycarbonates, acrylics, methacrylics, phosphazenes, siloxanes, vinyls, homopolymers, and copolymers thereof.

15. The method of claim 13 wherein the first polymer matrix comprises a polysiloxane.

16. The method of claim 1 wherein the optical element is an intraocular lens.

17. The method of claim 1, wherein the refraction modulating composition comprises a photoinitiator and one or more monomers of the general formula:

wherein Y is one of either:

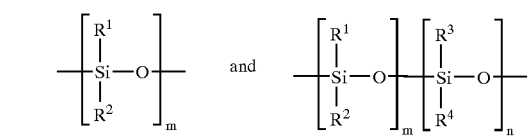

wherein m and n are independently each an integer and $R^1$, $R^2$, $R^3$, and $R^4$, are independently each hydrogen, alkyl (primary, secondary, tertiary, cyclo), aryl, and heteroaryl; X and $X^1$ are:

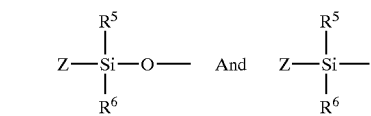

respectively wherein $R^5$ and $R^6$ are independently each hydrogen, alkyl, aryl, or heteroaryl; and Z is a photopolymerizable group.

18. The method of claim 17 wherein $R^1$, $R^2$, $R^3$, $R^4$, $R^5$ and $R^6$ are each independently a $C_1$–$C_{10}$ alkyl or phenyl and Z is selected from the group consisting of acrylate, allyloxy, cinnamoyl, methacrylate, stebenyl and vinyl.

19. The method of claim 18, wherein the step of exposing at least a portion of the lens to a stimulus (b) results in a change in the optical properties of the lens.

20. The method of claim 18 wherein the step of exposing the same or different portion of the lens to stimulus (d) results in a change in the optical properties of the lens.

21. The method of claim 18 further comprising repeating steps (b) through (d) until a desired change in optical properties is achieved.

22. The method of claim 18 wherein the intraocular lens further comprises a first polymer matrix.

23. The method of claim 18 wherein the refraction modulating composition comprises a siloxane.

24. The method of claim 18 wherein the refraction modulating composition comprises a photoinitiator and one or more monomers of the general formula:

wherein Y is one of either:

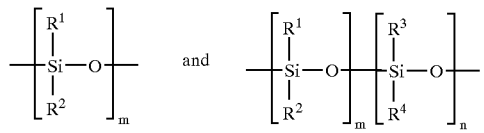

wherein m and n are independently each an integer and $R^1$, $R^2$, $R^3$, and $R^4$, are independently each hydrogen, alkyl (primary, secondary, tertiary, cyclo), aryl, and heteroaryl; X and $X^1$ are:

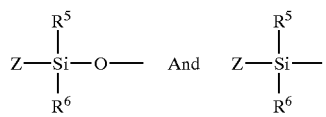

respectively wherein $R^5$ and $R^6$ are independently each hydrogen, alkyl, aryl, or heteroaryl; and Z is a photopolymerizable group.

25. The method of claim 17 wherein $R^1$, $R^2$, $R^3$, and $R^5$ and $R^6$ are independently selected from the group consisting of methyl, ethyl and propyl and $R^4$ is phenyl.

26. The method of claim 17 wherein the monomer is selected from the group consisting of (i) dimethysiloxane-dephenylsiloxane copolymer end capped with a vinyldimethysilane group, (ii) dimethylsiloxane-methylphenylsiolxane copolymer end capped with a methacryloxy propyldimethylsilene group, and (iii) dimethylsiloxane end capped with a methacryloxypropylldimethylsiloxane group.

27. The method of claim 1 further comprising the step of exposing the entire lens to a stimulus.

28. A method of implementing an adjustable intraocular lens comprising:

(a) implanting an intraocular lens in a patient, the adjustable intraocular lens comprising a refraction modulating composition dispersed therein, the refraction modulating composition being capable of stimulus induced polymerization;

(b) exposing at least a portion of the intraocular lens to a stimulus;

(c) waiting an interval of time;

(d) exposing a different or same portion of the intraocular lens to a stimulus.

29. The method of claim 28 wherein the stimulus is light.

30. The method of claim 29 wherein the changes in optical properties is induced by the stimulus induced polymerization of the refraction modulating composition.

31. The method of claim 28 wherein the stimulus in ultraviolet light.

32. The method of claim 28 wherein the refraction modulating composition is capable of photo-induced polymerization.

33. The method of claim 32 wherein the change in optical properties is induced by the stimulus induced polymerization of the refraction modulating composition.

34. The method of claim 33 wherein the first polymer matrix is selected from the group consisting of homopolymers and copolymers of siloxanes, acrylates, methacrylates, phosphazenes and vinyls.

35. The method of claim 32 further comprising the step of exposing the entire lens to a stimulus once the desired optical properties are achieved.

* * * * *

UNITED STATES PATENT AND TRADEMARK OFFICE
CERTIFICATE OF CORRECTION

| | |
|---|---|
| PATENT NO. | : 6,824,266 B2 |
| APPLICATION NO. | : 10/358065 |
| DATED | : November 30, 2004 |
| INVENTOR(S) | : Jethmalani et al. |

It is certified that error appears in the above-identified patent and that said Letters Patent is hereby corrected as shown below:

On the Title Page

Item (56) References Cited
Other Publications

Delete "PCT Written Opinion dated May 17, 2001 from corresponding International Application No. PCT/US99/23728 filed Oct. 18, 1999",
Insert -- PCT Written Opinion dated May 17, 2001 from corresponding International Application No. PCT/US99/23728 filed Oct. 13, 1999--

Item (56) References Cited
Foreign Patent Documents

Delete "WO WO-93/21245 Al 2/1993",
Insert --WO WO-93/21245 Al 10/1993--

Item (56) References Cited
Other Publications

Delete "American National Standard for Safe Use of Lasers: B Criteria for Exposures of Eye and Skin; American National Standard; 1993; pp. 31-43; Laser Insitute",
Insert -- American National Standard for Safe Use of Lasers: 8 Criteria for Exposures of Eye and Skin; American National Standard; 1993; pp. 31-43; Laser Institute--

Item (56) References Cited
Other Publications

Delete "Fouassier et al.; Visible Lasers Lights",
Insert --Fouassier et al.; Visible Laser Lights--

Item (56) References Cited
Other Publications

Delete "Kunzler; Silicon",
Insert --Kunzler; Silicone--

Item (56) References Cited
Other Publications
Lai et al., Synthesis and Characterization of...

Delete "1773-1783",
Insert --1773-1782--

Item (56) References Cited
Other Publication
Longhurst; Chapter XV - The Monochromatic...

Delete "Abberrations",
Insert --Aberrations--

UNITED STATES PATENT AND TRADEMARK OFFICE
CERTIFICATE OF CORRECTION

PATENT NO. : 6,824,266 B2
APPLICATION NO. : 10/358065
DATED : November 30, 2004
INVENTOR(S) : Jethmalani et al.

It is certified that error appears in the above-identified patent and that said Letters Patent is hereby corrected as shown below:

On the Title Page (cont'd)

| | |
|---|---|
| Item (56) References Cited Other Publications | Delete "Monroe; Photoinitiators", Insert --Monroe, et al.; Photoinitiators-- |
| Item (56) References Cited Other Publications | Delete "Steinert et al.; Long-term clinical results of AMO PhacoFlex model SI-18 introcular", Insert --Steinert et al.; Long-term clinical results of AMO PhacoFlex model SI-18 intraocular-- |

In the Claims

| | |
|---|---|
| Column 18, line 1, Claim 2 | Delete "claims", Insert --claim-- |
| Column 18, line 12, Claim 6 | Delete "(C)", Insert --(c)-- |
| Column 20, line 3, Claim 26 | Delete "dephenylsiloxane", Insert --diphenylsiloxane-- |
| Column 20, line 5, Claim 26 | Delete "methylphenylsiolxane", Insert --methylphenylsiloxane-- |
| Column 20, line 6, Claim 26 | Delete "propyldimethylsilene", Insert --propyldimethylsilane-- |
| Column 20, lines 7-8 | Delete "methacryloxypropylldimethylsiloxane", Insert --methacryloxypropyldimethylsiloxane-- |

UNITED STATES PATENT AND TRADEMARK OFFICE
CERTIFICATE OF CORRECTION

PATENT NO. : 6,824,266 B2
APPLICATION NO. : 10/358065
DATED : November 30, 2004
INVENTOR(S) : Jethmalani et al.

It is certified that error appears in the above-identified patent and that said Letters Patent is hereby corrected as shown below:

In the Claims (cont'd)

Column 20, line 27, Claim 31    Delete "the stimulus in",
                                Insert --the stimulus is--

Signed and Sealed this

Twenty-first Day of August, 2007

JON W. DUDAS
*Director of the United States Patent and Trademark Office*